(12) United States Patent
Lenoir

(10) Patent No.: US 8,110,539 B2
(45) Date of Patent: Feb. 7, 2012

(54) ENZYME STABILIZATION

(75) Inventor: Pierre Marie Lenoir, Richterswil (CH)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/045,036

(22) Filed: Mar. 10, 2011

(65) Prior Publication Data

US 2011/0166057 A1 Jul. 7, 2011

Related U.S. Application Data

(63) Continuation of application No. 11/297,697, filed on Dec. 8, 2005, now Pat. No. 7,928,052.

(60) Provisional application No. 60/634,564, filed on Dec. 9, 2004.

(51) Int. Cl.
| | |
|---|---|
| *C11D 3/37* | (2006.01) |
| *C11D 3/00* | (2006.01) |
| *C11D 7/42* | (2006.01) |
| *C11D 17/00* | (2006.01) |
| *C11D 17/08* | (2006.01) |
| *C11D 3/20* | (2006.01) |
| *D06L 1/02* | (2006.01) |
| *D06L 1/04* | (2006.01) |
| *C12S 11/00* | (2006.01) |
| *C12S 9/00* | (2006.01) |

(52) U.S. Cl. ........ 510/392; 510/276; 510/280; 510/283; 510/291; 510/320; 510/321; 510/337; 510/393; 510/405

(58) Field of Classification Search .......... 510/276, 510/280, 283, 291, 320, 321, 337, 392, 393, 510/405
See application file for complete search history.

(56) References Cited

U.S. PATENT DOCUMENTS

| | | | | |
|---|---|---|---|---|
| 4,842,758 A | * | 6/1989 | Crutzen | 510/321 |
| 5,629,278 A | * | 5/1997 | Baeck et al. | 510/236 |
| 5,691,292 A | * | 11/1997 | Marshall et al. | 510/221 |
| 5,834,415 A | * | 11/1998 | Nielsen et al. | 510/392 |
| 2005/0197270 A1 | * | 9/2005 | Kaasgaard | 510/392 |

OTHER PUBLICATIONS

R. Pizer and R. Selzer. "The Boric Acid/Lactic Acid System, Equilibria and Reaction Mechanism" Inorg. Chem. 23, 1984, 3023-3026.*

* cited by examiner

*Primary Examiner* — Lorna M Douyon
*Assistant Examiner* — Tanisha Diggs

(57) ABSTRACT

A method is disclosed for stabilizing liquid enzyme-containing liquid formulations by adding at least one boron compound and at least one alpha-hydroxy-mono-carboxylic acid or the salt of an alpha-hydroxy-mono-carboxylic acid capable of forming an enzyme-stabilizing compound. An enzyme-stabilized formulation is disclosed comprising an alpha-hydroxy-mono-carboxylic acid or the salt of an alpha-hydroxy-mono-carboxylic acid, a boron containing compound capable complexing with an alpha-hydroxy-mono-carboxylic acid, the complex formed by the boron compound and the an alpha-hydroxy-mono-carboxylic acid, and an enzyme. The invention applies to both enzyme concentrate raw materials, and to useful product formulations.

4 Claims, 4 Drawing Sheets

ENZYME STABILIZATION

CROSS REFERENCE TO RELATED APPLICATIONS

This application is a continuation of U.S. patent application Ser. No. 11/297,697, filed Dec. 8, 2005 now U.S. Pat. No. 7,928,052, which claims the benefit of U.S. Provisional Application Ser. No. 60/634,564, filed Dec. 9, 2004.

FIELD OF THE INVENTION

This invention relates to stabilization and the reversible inhibition of enzymes, including proteases, in liquid compositions, and more particularly to liquid enzyme-containing formulations having an enzyme stabilization system comprising a complex formed from a boron-containing compound and an alpha-hydroxy mono-carboxylic acid.

BACKGROUND OF THE INVENTION

Enzymes, which are produced by, and are obtained from, living cells (e.g., bacteria), have become a common component in various compositions, including industrial and consumer applications and cleaning compositions, such as laundry detergents, laundry presoak and pretreatment products. Enzyme compositions are used to break down organic materials such as proteins, starches and fats into smaller molecules that can be more easily solubilized or dispersed in an aqueous liquid. Some uses for enzyme compositions for cleaning include laundry detergents, fabric softeners, all types of wipes, liquid dishwashing products (manual or automatic), and hard surface cleaners. Enzymes for use in personal care formulations include facial, skin and body care products, where proteases enhance various macromolecular maturation or hydrolytic functions. Enzymes are used for a variety of bio-processing uses such as converting grains into sweeteners, fermentation, converting biomass into ethanol for fuel, and enhancing animal feed for livestock and pets. In the pulp and paper industries, xylanases are used for bleach boosting, cellulases for refining pulp and paper recycling, and amylases for starch removal and modification. Other industrial uses of enzymes include the industrial biotech production of chemical products, plastics and fibers. Enzymes have also been developed for the bioremediation of industrial and agricultural wastes, decontamination of chemical toxins, and maintenance of processes by biofilm removal.

The largest volume of enzymes is currently for use in detergents and cleaners, where detergent enzymes generally exhibit hydrolytic activity under alkaline conditions. Detersive compositions frequently contain active proteases (i.e., proteolytic enzymes); they also may contain amylolytic enzymes that break down starch-containing soils. Other enzymes compositions use lipase enzymes or cellulolytic enzymes, typically in combination with a protease or amylase. Although detergent formulators select these enzymes for their ability to remain active in aqueous detersive systems, the proteolytic, amylolytic and other enzymes commonly employed in detersive compositions may exhibit loss of activity (i.e., instability) during storage.

The loss of enzyme activity is more pronounced in liquid or gel compositions. Enzymes may be destabilized by unfolding of the three-dimensional structure of the enzyme or by enzyme breaking down. Common destabilizers include polar solvents like of water or other solvents, microbial attack, electrolytes, charged surfactant, temperature and extreme pH. Stabilizers are added to rigidify the structure of the enzymes include boric acid, glycols, small organic acids, and calcium chloride. In addition, proteases have a tendency to attack themselves and other enzymes, causing autolysis and proteolysis in the formulation. Formulators inhibit protease with protease inhibiting materials such as boric acid, boronic acids, proteinaceous materials, borate esters of vicinal polyols, for example monopropylene glycol with sodium borate In order to compensate loss of enzyme activity during periods of storage, formulators may use excess enzymes in liquid enzymatic compositions such as detergents. However, enzymes are relatively expensive formulation ingredients; accordingly, formulators may employ enzyme stabilizers in liquid compositions to inhibit autolysis of the protease and other enzyme destabilization reactions.

Materials that have been used for stabilizing enzymes include various organic and inorganic compounds such as polyols, carboxylic acids, carboxylic acid salts, carboxylic acid esters, and sugars; calcium salts; boron compounds, and various combinations thereof. Protein extracts can also be used to stabilize enzymes through inhibition of the enzyme.

U.S. Pat. No. 5,221,495 discloses a three-component enzyme stabilization system for liquid detergent compositions including a boron compound, a hydroxypolycarboxylic acid having two or three carboxylic acid groups and from 1 to 4 hydroxyl groups, and a calcium salt. The hydroxypolycarboxylic acid is preferably citric acid.

U.S. Pat. No. 4,842,758 discloses detergent compositions containing an enzyme that is stabilized by a combination of ingredients, including an alpha-hydroxy-carboxylic acid or an alpha-hydroxy-poly-carboxylic acid, a boron compound, and a proteinaceous material, e.g., casein. The patent discloses as examples maleic acid, tartaric acid, lactic acid, and citric acid, with citric acid being most preferred. This patent teaches that the proteinaceous material is essential to inhibit the protease and thus stabilizes both the protease and amylase enzymes. This patent teaches that, without the proteinaceous material, it is impossible to stabilize the enzymes used in the system. The amount of proteinaceous material in the compositions is relatively high, at 1 to 6 wt. %, compared to 1 to 5 wt. % of alpha-hydroxy carboxylic acid, and 0.5 to 2.5 wt. % of boron and 0.5 to 3 parts by weight enzyme. This patent teaches mixing alpha-hydroxy-acid with Borax ($Na_2B_4O7.10H2O$), adding casein dissolved in NaOH solution, and then adding this mixture to the enzyme. Furthermore, this patent teaches the use of phosphate salt builders in levels in excess of 5%.

U.S. Pat. No. 5,691,292 describes a dishwashing detergent composition containing an active enzyme and an enzyme stabilization system comprising at least one stabilizing agent selected from the group consisting of calcium ion, boric acid, propylene glycol, short chain carboxylic acids, boronic acid, polyhydroxyl compounds and mixtures thereof. It is disclosed that suitable polyols contain from about 2 to about 6 carbon atoms and from about 2 to about 6 hydroxyl groups. The patent teaches specific examples such as propylene glycol, with 1,2-propane diol being preferred, 1,2-butane diol, ethylene glycol, glycerol, sorbitol, mannitol and glucose. The patent also teaches the option of adding carboxylates, including formates, to the compositions, and that sodium formate is preferred. The patent also teaches the option of adding detergency builders such as citric acid or an alkali metal citrate (e.g., sodium citrate) to the dishwashing detergent compositions. The patent includes sodium citrate (as a detergency builder), and an enzyme stabilization system consisting of one or more of the following ingredients: boric acid, 1,2- propane diol, calcium formate and sodium formate as an exemplary dishwashing detergent compositions.

U.S. Pat. No. 4,462,922 describes an aqueous enzymatic liquid detergent composition containing an enzyme stabilization system. The enzyme stabilization system comprises boric acid or an alkali-metal borate, a polyol, and an antioxidant that is a reducing alkali-metal salt. This patent teaches that the polyols that can be used contain from 2 to 6 hydroxyl groups. The listed polyols are ethylene glycol, propylene glycol, 1,2-propane diol, butylene glycol, hexylene glycol, glycerol, mannitol, sorbitol, erythritol, glucose, fructose, lactose and erythritan.

U.S. Pat. No. 5,468,414 discloses liquid detergent compositions containing an alpha-hydroxy acid builder, a surfactant, a proteolytic enzyme, a second enzyme, and an enzyme stabilization system comprising a mixture of certain vicinal polyols and boric acid or its derivatives. This patent teaches built liquid detergent compositions containing an alpha-hydroxy acid builder such as tartrate mono-succinic acid or citric acid. This patent teaches that alpha-hydroxy acid builders are detrimental to enzymes stability, consequently, they teach use of specially selected vicinal polyols in combination with boric acid or its derivatives as an enzyme stabilization system.

U.S. Pat. No. 5,976,556 describes skin conditioning compositions containing an acid protease which is enzymatically active below about pH 5.5 and which is significantly inactive at or above pH 5.5, and an acidic buffer comprising an inorganic acid. This patent teaches the uses of organic acids including alpha-hydroxycarboxylic acids such as lactic acid, citric acid, glycolic acid and malic acid to reduce skin pH, but does not teach an enzyme-stabilizing complex.

SUMMARY OF THE INVENTION

I have discovered that combining certain boron compounds with alpha-hydroxy-mono-carboxylic acids or their salts at certain pH ranges forms complexes that, surprisingly, greatly improve stability of enzyme-containing liquid compositions. The preferred complexes are 1:1 boron to alpha hydroxy groups and have a single, negative charge, represented by [1:1]$^-$. The enzyme stabilization compositions and methods of this invention works by providing three-dimensional stabilization of enzymes, therefore improving shelf-life of even very dilute enzymatic compositions in water. In addition, the composition and methods of this invention reversibly inhibit proteolytic activity to stabilize enzymes, to and improve shelf life of various liquid formulations containing proteases. Therefore, "enzyme stabilization" and "enzyme-stabilized" in this invention refers both to three-dimensional stabilization and to reversible inhibition of the enzyme. This is of special interest when the enzyme is a protease. My invention will stabilize both liquid enzyme concentrates used as raw materials and enzyme-containing liquid product formulations such as detergents. The enzyme stabilization method of this invention allows formulators to decrease levels of enzyme stabilizers, or decrease levels of enzymes, therefore providing meaningful cost savings. In addition, my invention is effective without additional protein compounds, and with little or no glycol materials.

The enzyme-containing liquid compositions of the present invention include both enzyme raw materials containing about 0.01 to 25 wt. % active enzyme, and enzyme-containing liquid formulations with as little as 0.0001 wt. % active enzyme. Enzyme concentrates are used as raw materials by formulators, while enzyme-containing liquid formulations include, for example, personal care products, medical products, household products, institutional or industrial products.

One aspect of the invention provides improved intrinsic enzyme activity by stabilizing the three-dimensional structure thus providing, for example, improved cleansing action in detergent formulations. Another aspect of this invention is that the enzyme stabilizing combination may prevent protease in an enzyme composition from autolysis and from proteolysis by inhibiting proteolytic activity of proteases.

Another aspect of my invention is that the method and compositions are useful when enzyme-containing liquid formulations also contain boron scavengers such as glycerol, mono-propylene glycol, some surfactants such as poly-hydroxy fatty amides, and alpha-hydroxy-poly-carboxylic acids such as citric acid. The complex formed by the alpha-hydroxy-mono-carboxylic acid with boron is active in low amounts. Formulators can use less boron in the liquid enzyme-containing formulation. This is helpful in applications or locations where there is a trend to lower the boron content, for example for environmental concerns.

Another aspect of this invention is that the combination of an alpha-hydroxy-mono-carboxylic acid, a boron compound, and a [1:1]$^-$ complex of the alpha-hydroxy-mono-carboxylic acid stabilizes enzymes even when substantially free of non-enzymatic proteinaceous material, such as casein, taught in the prior art. By substantially free, I mean less than 1 wt. % of such a proteinaceous protein.

DESCRIPTION

Figure 1:
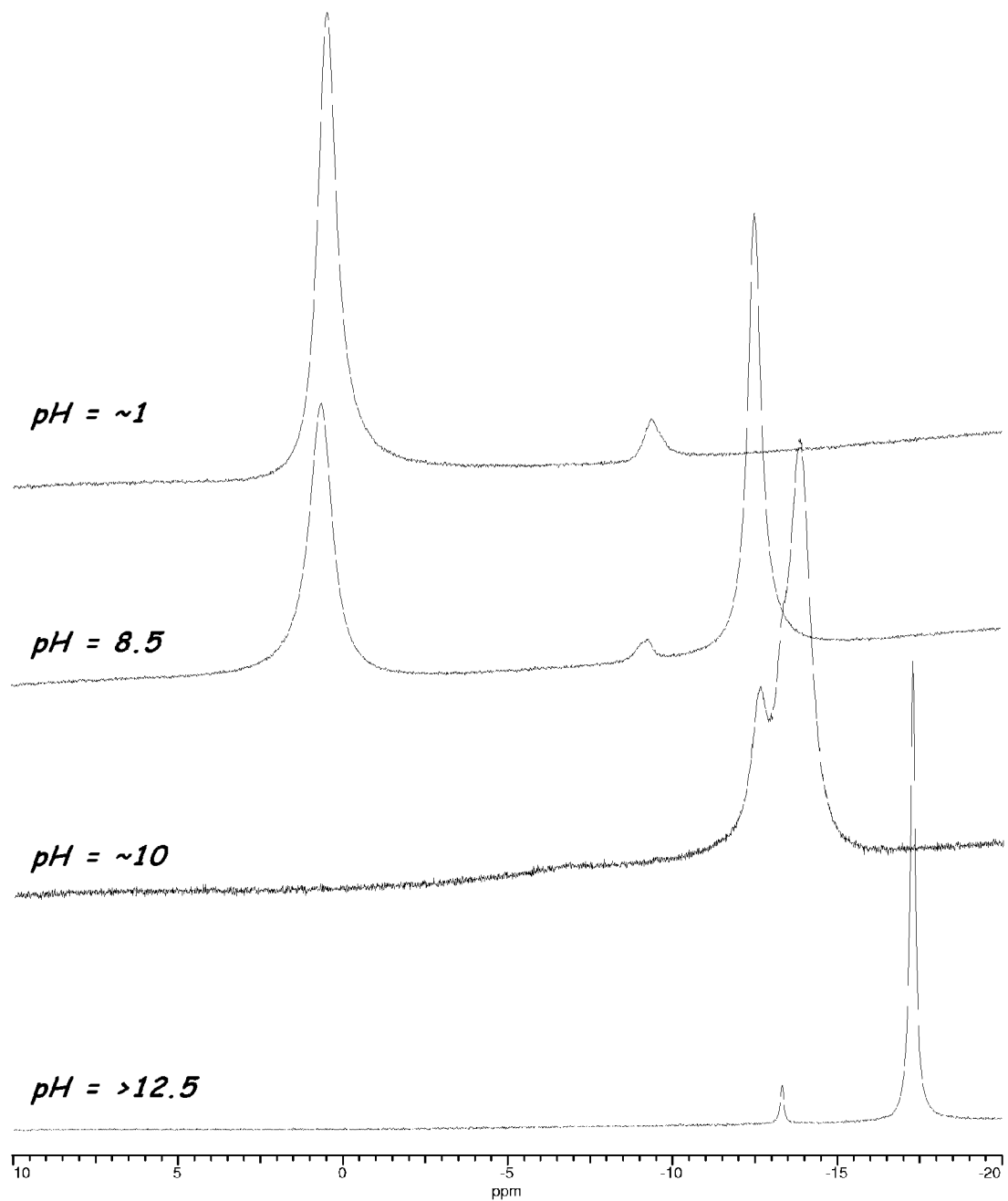
FIG. 1 shows the peaks for various boron compounds from $^{11}$B-NMR testing on four different pH solutions formed from a 0.2:0.2 ratio of boric acid to lactic acid.

One aspect of this invention relates to use of a formulations containing a combination of an alpha-hydroxy-mono-carboxylic acid or salt of an alpha-hydroxy-mono-carboxylic acid, a boron-containing compound, and a complex formed from the alpha-hydroxy-mono-carboxylic acid and the boron-containing compound to stabilize enzyme formulations. This invention provides more effective three-dimensional structure enzyme stabilization, enzyme (protease) inhibition, and enzyme stabilization in both enzyme raw material concentrates and enzyme-containing product formulations, including detergents. An enzyme-stabilizing combination of this invention may inhibit proteolytic activity of proteases, in particular, more effectively than previous enzyme stabilizers. This invention has the advantage of allowing formulators to use lower amounts of enzymes or other enzyme stabilizing agents, and therefore lower the cost liquid formulations containing proteases.

Another aspect of the present invention is an enzyme-stabilized composition comprising:
(a) an alpha-hydroxy-mono-carboxylic acid or a salt of an alpha-hydroxy-mono-carboxylic acid capable of complexing a boron compound to form a complex that has stabilizing properties for enzymes, and (b) a boron compound capable of complexing an mono-alpha hydroxy-carboxylic acid (or its salt) to form a complex that has stabilizing properties for enzymes; and
(c) an anionic complex formed by (a) and (b); and
(d) an enzyme.

The term alpha-hydroxy-mono-carboxylic acid, in the present invention, refers to any compound that contains an alpha-hydroxy-mono-carboxylic acid or carboxylate functional group. Unless otherwise stated, the term alpha-hydroxy-mono-carboxylic acid also refers to the salts of such acids. The alpha-hydroxy-mono-carboxylic acid may be represented by the formula R—C(OH)(R')—C(O)—OH; wherein R is selected from a hydrogen atom, the group consisting of $C_1$ to $C_{10}$ alkyl, aryl, substituted $C_1$ to $C_{10}$ alkyl, substituted aryl, nitro, ester, ether, amine, amine derivative, substituted amine and substitutions on the alkyl or aryl groups is selected from aryl or alkyl groups, nitro, nitro derivative, hydroxyl, hydroxyl derivative, ester, ether, amine, amine derivative, substituted amine, amide, amide derivative and halogen; and R' is selected from a hydrogen atom, the group consisting of $C_1$ to $C_{10}$ alkyl, aryl, substituted $C_1$ to $C_{10}$ alkyl, substituted aryl, nitro, ester, ether, amine, amine derivative, substituted amine, and substitutions on the alkyl or aryl groups is selected from aryl or alkyl groups, nitro, nitro derivative, hydroxyl, hydroxyl derivative, ester, ether, amine, amine derivative, substituted amine, amide, amide derivative and halogen. Preferably, R and R' each have a molecular weight of less than 300. When R is different from R', the carbon atom in alpha position of the acid function is optically active and the different optical isomers are also considered (e.g. D-, L-, DL-alpha hydroxy acid).

Non-limiting examples of alpha-hydroxy-mono-carboxylic acids that may be used to complex with boron for inhibiting enzymes such as the inhibition of the proteolytic activity (e.g., protease autolysis and/or proteolysis of non-proteolytic enzymes) or used for stabilizing enzymes in enzyme-containing liquid formulations include lactic acid, mandelic acid, glycolic acid, hydroxy butyric acid, and hydroxy isobutyric acid and any of their optical isomers where applicable. In some environments, such as commercial heavy-duty liquid detergent compositions, such a complex is more likely to take place between the salt of an alpha-hydroxy-mono-carboxylic acid and boric acid. Another aspect of this invention is that a complex of mono-alpha hydroxy acid or salt of it and a boron compound is more efficient for stabilizing and inhibiting enzymes than systems using, for example, diols with borate.

The boron compounds that may be used in the present invention are those that are water-soluble and that, when added to water, form boric acid or an alkali metal salt of boric acid. Suitable but non-limiting boron compounds of the present invention are cited in patent application WO 92/19709. Boron compounds that may be employed include boric acid, boric oxide, and/or alkali metal borates. Suitable alkali metal borates include sodium and potassium ortho-, pyro-, and meta-borates, polyborates, and borax ($Na_2B_4O_7.10H_2O$). Preferred boron-containing compounds include boric acid, sodium borate (Na3BO3), other inorganic salts and organic salts of boron, and borax. When used without the complex of the present invention, the amount of boron-containing compound that is effective to enhance enzyme stability in a liquid enzyme-concentrate, or in a liquid detergent composition, is an amount equivalent 0.1% to 10% boric acid, by weight. In this invention, however, because the boron compound is forming a complex with a alpha-hydroxy-mono-carboxylic acid or its salt, the amount of boron will be determined relative to the amount of the alpha-hydroxy-mono-carboxylic acid or its salt, taking into account any boron scavengers and the amount of enzymes to stabilize in the formulation. As a result, the amount of total boron compound in a liquid enzyme-containing composition may be lower than comparable prior art compositions. Therefore, a preferable range of boron concentration, expressed as boric acid, in an enzyme-containing composition from 0.1 to 5 wt. % and more preferably 0.1 to 1.5 wt. % in an enzyme-containing product formulation.

In another aspect of this invention, a boron-containing compound forms a complex with a mono-alpha hydroxy carboxylic acid or its salt in order to improve enzyme stability. The anionic complex may be represented by the general formula:

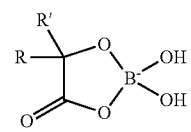

wherein R is selected from a hydrogen atom, the group consisting of $C_1$ to $C_{10}$ alkyl, aryl, substituted $C_1$ to $C_{10}$ alkyl, substituted aryl, nitro, ester, ether, amine, amine derivative, substituted amine and substitutions on the alkyl or aryl groups is selected from aryl or alkyl groups, nitro, nitro derivative, hydroxyl, hydroxyl derivative, ester, ether, amine, amine derivative, substituted amine, amide, amide derivative and halogen; and R' is selected from a hydrogen atom, the group consisting of $C_1$ to $C_{10}$ alkyl, aryl, substituted $C_1$ to $C_{10}$ alkyl, substituted aryl, nitro, ester, ether, amine, amine derivative, substituted amine, and substitutions on the alkyl or aryl groups is selected from aryl or alkyl groups, nitro, nitro derivative, hydroxyl, hydroxyl derivative, ester, ether, amine, amine derivative, substituted amine, amide, amide derivative and halogen.

The formation of a complex between a boron-containing compound and an alpha-hydroxy-mono-carboxylic acid or its salt is an equilibrium reaction. Therefore, an enzyme-stabilizing combination of the present invention may contain an alpha-hydroxy-mono-carboxylic acid, a boron-containing compound (capable of forming boric acid), and a complex containing both boron and an alpha-hydroxy-mono-acid complex with the boron-containing compound. The pH, temperature, the complexation rate to form the active complex, complexation rate of any secondary complexes, the amount of ingredients added, and the presence of boron scavengers and the enzyme levels are some of the factors that may affect the amount of each component.

The complex formed has affinity with the active site of the enzyme and with the sub-sites around the active site of the enzyme. Without being bound to theory, I believe that the mono-complex, an anion with one mole of boron to one mole of alpha-hydroxy-mono-carboxylic groups, designated as $[1:1]^-$, stabilizes enzymes by adsorbing on the surface of enzymes and inhibits enzymes by binding into the active site of the enzyme. A di-complex having a 1:2 ratio of boron atoms to alpha-hydroxy-mono-carboxylic groups would have little or no effectiveness in stabilizing enzymes because it would not attach to or bind the enzyme.

One embodiment of my invention includes adding lactic acid and boric acid to liquid enzyme compositions between pH 2 and 10, preferably between pH 3 and pH 9, and the more preferred range is between pH 4 and pH 9, so that a $[1:1]^-$ complex is formed.

The equilibria of boron compounds with alpha-hydroxy mono carboxylic acids have been studied. Complexation constants are often referred as K1 and K2. For example, Pizer et al. "The Boric Acid/Lactic Acid System. Equilibria and Reaction Mechanism" *Inorg. Chem.* 1984, 23, 3023-3026 studied the reaction of boric acid, B(OH)3, with lactic acid CH—$_3$CH(OH)COOH to produce anionic complexes of both 1:1 and 1:2 stoichiometry. Pizer et al., describe the equilibria for the first two complexations as follows: $B(OH)_3 + H_2L \leftrightarrows [1:1]^- + H_3O^+$, $K_1 = 1.8 \times 10^{-3}$; $[1:1]^- + H_2L \leftrightarrows [1:2]^- + 2H_2O$, $K_2 = 6.6 \times 10 M^{-1}$, all where $H_2L$ is fully protonated lactic acid. At pH 4 to about pH 10, however, the first complexation reaction dominates over the second complexation with the lactic acid having lost a proton: $B(OH)_3 + HL^{--} \leftrightarrows [1:1]^- + H_2O$, $K_1' = 9.0 M^{-1}$. In addition, in the range of pH4 to pH10, the formation of a $[1:2]^-$ is low because the $[1:1]^-$ would have to complex with an hydroxy acid anion; the probability of reacting two negative anions is low. Therefore, this work suggests that, for lactic acid, the formation of the $[1:2]^-$ complex is strongly favored at pH between 2 and 4, while the $[1:1]^-$ complex is formed between about pH 2 to about pH 10, and most prevalent between about pH 3 and pH 9. Above about pH 9.15, the borate anion $B(OH)4^-$ begins to predominate in solution, and tends not to form a complex with an alpha-hydroxy anion.

A more general statement of the pH range for forming the complex of the present invention can be expressed as follows: if the pKa of the mono-alpha-hydroxy-carboxylic acid is denoted as $pKa_{AHA}$, and the pKa of boron compound is $pKa_B$, then the pH range of the formulation is desired to be from $pKa_{AHA}$ minus 2 points, up to $pKa_B$ plus 2 points. A more preferred pH range is from the $pKa_{AHA}$ minus 1.5 points up to the $pKa_B$ plus 1.5 points. An even more preferred range is from the $pKa_{AHA}$ minus one point, up to the $pKa_B$ plus one point. For simplicity, as the $pKa_{AHA}$ of the alpha-hydroxy-mono-carboxylic acids of the invention will vary between about pH 3 and pH 4 and the $pKa_B$ of boric acid is about 9.14, it is therefore convenient to refer to specific pH ranges, which are easily monitored.

Another factor in determining a preferred pH in the compositions of the present invention is the pH is the tolerance and activity domain of the enzymes. In most cases, and in particular for most liquid detergent compositions and liquid enzyme-concentrates added to detergent formulations, the enzyme or enzymes are enzymatically active at a pH above 5.5, and more particularly, exhibit peak activity above a pH of 5.5, and more preferably above a pH of 7.0.

I have also found that the amount of mono- or di-complex formed also depends on the ratio of boron compound to alpha-hydroxy-mono-carboxylic acid used in the formulation. The $[1:2]^-$ can form more easily if a large excess of lactic acid is used. This is demonstrated in the NMR samples of Example 5, below. In this NMR data, the domain for the mono- and di-complexes is slightly different, showing that the formation of the di-complex is concentration dependent.

The moles of acid needed for each mole of $[1:1]^-$ complex formed can be estimated based on the alpha-hydroxy-mono-carboxylic acid (or salt) and boron compounds selected, the pH of the liquid enzyme containing composition, the levels of enzymes and the amount of boron scavengers present. Therefore, the amount of alpha-hydroxy-mono-carboxylic acid (or its salt) added will depend both on the amount of boron compound to be complexed and the amount of enzyme to be inhibited or stabilized. The amount of boron compound added is similarly determined by the amount of alpha-hydroxy-mono-carboxylic acid or its salt; in addition, the amount of boron may be adjusted based on pH and on the amount of material that are boric acid scavengers, such as glycols, polyhydroxyl fatty amides, or alpha-hydroxyl poly carboxylic acid builders (i.e. citric acid). The molar ratio of mono-alpha hydroxy carboxylic acid to boron compound in this invention is 1:100 to 100:1. The molar ratio of the complex formed by the mono-alpha hydroxy carboxylic acid and the boron to the enzyme present in the range of 1:1 to 500:1. However, it is more economical to use less complex, and preferably the molar ratio of complex of this invention to the molar ratio of the enzymes is in the range of 1:1 to 100:1. As a starting point, the amount of alpha-hydroxy-mono-carboxylic acid in a formulation can range from 0.01 to 25 wt. %. More preferably, the alpha-hydroxy-mono-carboxylic acid will be from 0.1 to 10 wt. %.

Another aspect of my invention is the ability to use lower boron levels to stabilize enzyme compositions, compared to the prior art. The $[1:1]^-$ complex of this invention will stabilize enzymes and/or reversibly inhibit enzymes such as proteases more efficiently than a system using a combination of diols and borate. For example, most non-phosphate built heavy-duty detergents have a pH around 8-8.5, and use enzyme inhibitors made of vicinal diols and boron compounds at a relatively high level to provide adequate enzyme stabilization and (protease) reversible inhibition. When lower amounts of boron-scavengers such as diols, polyhydroxy based surfactants or alpha-hydroxy-poly-carboxylic acids are used, lower amounts of boron are needed in the overall composition.

This invention makes use of alpha-hydroxy-mono-carboxylic acids for complexing boron. Alpha-hydroxy-poly-carboxylic acids, such as citric acid, for instance, a common builder for detergents, does form a complex with boron, and is often used with enzyme compositions. However at pH above about 5 the complex between citric acid salt and boric acid possesses two to three negative charges and thus is probably too hydrophilic to fit the hydrophobic pocket of the active site of the enzymes to be able to reversibly inhibit enzymes, especially proteases. Thus, at pH about 5 or above, citric acid is a boron scavenger which is detrimental to enzyme stability.

The liquid enzyme-containing compositions of this invention contain at least one enzyme. In principle, the invention provides stability for any class of enzymes, preferably those that are useful between pH 2 and pH 10. Non-limiting examples of enzymes include proteases, lipases, amylases and cellulases. Enzymes can be used at their art-taught levels, for example at levels recommended by suppliers such as Novozymes, Novo Nordisk, and Genencor. The enzyme-containing liquid compositions of the present invention include both enzyme raw materials containing about 0.01 to 25 wt. % active enzyme, and enzyme-containing liquid formulations with as little as 0.0001 wt. % active enzyme. Enzyme concentrates are used as raw materials by formulators, while enzyme-containing liquid formulations include, for example, personal care products, medical products, household products, institutional or industrial products. Typical levels in the compositions of the present invention of pure enzymes are from 0.0001% to 25%. This can be 0.01 to 25% for an enzyme raw material, or 0.0001 to 2.5% for an enzyme-containing formulation such as a typical detergent, by weight of the composition. Enzymes suitable for incorporation into the various compositions of the present invention can be selected from the group consisting of peroxidases, proteases, glucoamylases, amylases, xylanases, cellulases, lipases, phospholipases, esterases, cutinases, pectinases, keratanases, reductases, oxidases, phenoloxidases, lipoxygenases, ligninases, pullulanases, tannases, pentosanases, malanases, B-glucanases, arabinosidases, hyaluronidase, chondroitinase, dextranase, transferase, laccase, mannanase, xyloglucanases, derivatives thereof and mixtures thereof, of any suitable origin, such as vegetable, animal, bacterial, fungal and yeast origin. The enzymes of the present invention produced by chemically or genetically modified routants are included by definition, as are close structural enzyme variants. Non limiting examples of enzymes-containing compositions of this invention may contains the enzymes and their classes described in patent applications US 2005/0059567 A1, WO 2004/113484 A1 and WO 92/19709.

The enzyme stabilizing combination of this invention inhibits the activity of proteases. By protease, I mean any of various enzymes that have proteolytic activity, causing or catalyzing hydrolytic breakdown of proteins into simpler, soluble substances such as peptides and amino acids. In this invention, proteases include endopeptidases, which catalyze the hydrolysis of peptide bonds in the interior of a polypeptide chain or protein molecule, and exopeptidases, which catalyze the hydrolysis of single amino acids from the end of a polypeptide chain. Therefore, one aspect of this invention is a stabilized enzyme-containing composition containing proteases. Proteases can be of animal, vegetable or microorganism (preferred) origin. More preferred is a serine protease of bacterial origin. Purified or nonpurified forms of this enzyme may be used. Proteases produced by chemically or genetically modified routants are included by definition, as are close structural enzyme variants. Particularly preferred is bacterial serine proteolytic enzyme obtained from *Bacillus, Bacillus subtilis* and/or *Bacillus licheniformis*.

Suitable proteases include Alcalase*, Esperase*, Savinase* (preferred); Maxatase*, Maxacal* (preferred), and Maxapem* 15 (protein engineered Maxacal), and subtilisin BPN and BPN[1] (preferred) which are commercially available. Preferred proteolytic enzymes are also modified bacterial serine proteases, such as those described in European Patent Application Serial Number 87 303761.8, filed Apr. 28, 1987 (particularly pages 17, 24 and 98), and which is called herein "Protease B", and in European Patent Application 199,404, Venegas, published Oct. 29, 1986, which refers to a modified bacterial serine proteolytic enzyme which is called "Protease A" herein. Preferred proteolytic enzymes, then, are selected from the group consisting of Savinase, Esperase, Maxacal, BPN, Protease A, Protease B, and Protease C, and mixtures thereof.

Suitable lipases for use herein include those of bacterial, animal, and fungal origin, including those from chemically or genetically modified routants.

Suitable bacterial lipases include those produced by *Pseudomonas*, such as *Pseudomonas stutzeri* ATCC 19,154, as disclosed in British Patent 1,372,034, incorporated herein by reference. Suitable lipases include those which show a positive immunological cross-reaction with the antibody of the lipase produced the micro-organism *Pseudomonas fluorescens* IAM 1057. This lipase and a method for its purification have been described in Japanese Patent Application 53-20487, laid open on Feb. 24, 1978, which is incorporated herein by reference. This lipase is available under the trade name Lipase P "Amano," hereinafter referred to as "Amano-P." Such lipases should show a positive immunological cross reaction with the Amano-P antibody, using the standard and well-known immunodiffusion procedure according to Oucheterlon (Acta. Med. Scan., 133, pages 76-79 (1950)). These lipases, and a method for their immunological cross-reaction with Amano-P, are also described in U.S. Pat. No. 4,707,291, Thom et al., issued Nov. 17, 1987, incorporated herein by reference. Typical examples thereof are the Amano-P lipase, the lipase ex *Pseudomonas fragi* FERM P 1339 (available under the trade name Amano-B), lipase ex *Pseudomonas nitroreducens* var. lipolyticum FERM P 1338 (available under the trade name Amano-CES), lipases ex *Chromobacter viscosum* var. lipolyticum NRRlb 3673, and further *Chromobacter viscousm* lipases, and lipases ex *Pseudomonas gladioli*. Other lipases of interest are Areario AKG and *Bacillis* Sp lipase (e.g. Solvay enzymes).

Other lipases which are of interest where they are compatible with the composition are those described in EP A 0 339 681, published Nov. 28, 1990, EP A 0 385 401, published Sep. 5, 1990, EP A 0 218 272, published Apr. 15, 1987, and PCT/DK 88/00177, published May 18, 1989, all incorporated herein by reference.

Suitable fungal lipases include those produced by *Humicola lanuginosa* and *Thermomyces lanuginosus*. Most preferred is lipase obtained by cloning the gene from *Humicola lanuginosa* and expressing the gene in *Aspergillus oryzae* as described in European Patent Application 0 258 068, incorporated herein by reference, commercially available under the trade name Lipolase* from Novozymes. Additional examples can be found in US 2005/0059567, WO 2004/113484 A1 and WO 92/19709.

Any amylase suitable for use in a liquid detergent composition can be used in these compositions. Amylases include for example, a-amylases obtained from a special strain of *B. licheniforms*, described in more detail in British Patent Specification No. 1,296,839. Amylolytic enzymes include, for example, Rapidase*, Maxamyl*, Termamyl* and BAN*. Additional examples can be found in US 2005/0059567, WO 2004/113484 A1 and WO 92/19709.

The cellulases usable in the present invention include both bacterial and fungal cellulases. Preferably, they will have a pH optimum of between 5 and 9.5. Suitable cellulases are disclosed in U.S. Pat. No. 4,435,307, Barbesgoard et al., which discloses fungal cellulase produced from *Humicola insolens*. Suitable cellulases are also disclosed in GB-A-2.075.028; GB-A-2.095.275 and DE-OS-2.247.832.

Examples of such cellulases are cellulases produced by a strain of *Humicola insolens* (*Humicola grisea* var. thermoidea), particularly the *Humicola* strain DSM 1800.

Other suitable cellulases are cellulases originated from *Humicola insolens* having a molecular weight of about 50 KDa, an isoelectric point of 5.5 and containing 415 amino acids. Such cellulases are described in Co-pending European patent application No. 93200811.3, filed Mar. 19, 1993. Especially suitable cellulases are the cellulases having color care benefits. Examples of such cellulases are described in European patent application No. 91202879.2, filed Nov. 6, 1991 (Novo Nordisk). Additional examples are found in US 2005/0059567 A1, WO 2004/113484 A1 and WO 92/19709.

The method of making the enzymes for use in the compositions of this invention is not important to whether this invention works. In addition to genetic manipulations other methods for making enzymes by mutagenesis may be used such as site-directed mutagenesis, saturation mutagenesis, cassette mutagenesis, or directed enzyme evolution by recombinative or non-recombinative methods, for example.

Since method of this composition is most effective between 2 and 10, it is useful in applications operating in this pH range, such as animal feed, food handling and food processing, household, including fabric care and hard surface care, and personal care. Enzyme compositions of the present invention include those containing phytases, useful to increase the absorption or organic phosphorous from animal feed in agriculture applications. Similarly, compositions of the present invention include those containing xylanases and protease to improve nutrient release and absorption.

Other stabilized enzyme compositions of the present inventions are useful for the food industry for meat processing, fruit and vegetable processing areas, starch processing, beverages, baking, or dietary enzymes. Enzymes in such compositions include glutaminase for flavor enhancement, lactase, cellulase, amylases, and proteases.

Other stabilized enzyme compositions of the present invention are useful in personal care. For example, proteases, lipases and catalases are useful for contact lens cleaner, while glucoamylases and glucose oxidases are useful in toothpaste compositions. Enzyme compositions are useful in skin care, including washes and chemical peels.

Enzyme systems have additional uses in chemical and environmental applications for waste treatment sectors. Stabilized enzyme systems containing lipases, amylases, nitrlases, hydralases, glucosynthatases, and mono-oxygenases of the present invention have the advantage of improved storage time before use. Specialty chemical processes such as chiral synthesis use compositions containing hydrolases, in general, and lipases in particular.

The stabilized enzyme-containing compositions of this invention can be formulated into liquid compositions containing surfactants. The surfactants can be selected based on the use of the final composition, and include anionic surfactants, nonionic surfactants, cationic surfactants, amphophlytic surfactants, zwitterionic surfactants and mixtures of one or more of these surfactants. Non-limiting surfactants that may be used in the present invention are described in the following references: WO 92/19709, US 2005/0059567 A1, WO 2005/049776 A1, U.S. Pat. No. 6,803,355 B1, WO 2004/113484 A1, WO 2005/012474 A1. As an example, in a detergent or laundry formulation as an embodiment of the invention, the stabilized enzyme-containing compositions may contain from about 1% to about 60% by weight of at least one surfactant.

Anionic surface active agents which may be used in the present invention are those surface active compounds which contain a long chain hydrocarbon hydrophobic group in their molecular structure and a hydrophile group, i.e. water solubilizing group such as sulfonate or sulfate group. The anionic surface active agents include the alkali metal (e.g. sodium and potassium) water soluble higher alkyl benzene sulfonates, alkyl sulfonates, alkyl sulfates and the alkyl poly ether sulfates.

The higher alkyl polyether sulfates may be used with the present invention can be normal or branched chain alkyl and contain lower alkoxy groups which can contain two or three carbon atoms. The normal higher alkyl polyether sulfates are preferred in that they have a higher degree of biodegradability that the branched chain alkyl and the lower poly alkoxy groups are preferably ethoxy groups.

Nonionic synthetic organic detergents which can be used with the invention, alone or in combination with other surfactants are described below. As is well known, the nonionic synthetic organic detergents are characterized by the presence of an organic hydrophobic group and an organic hydrophillic group such as fatty acid glucose amide. Most nonionic surfactants are typically produced by the condensation of an organic aliphatic or alkyl aromatic hydrophobic compound with ethylene oxide (hydrophilic in nature).

Usually, the nonionic detergents are poly-lower alkoxylated lipophiles wherein the desired hydrophile-lipophile balance is obtained from addition of a hydrophilic poly-lower alkoxy group to a lipophilic moiety. A preferred class of the nonioinic detergent employed is the poly-lower alkoxylated higher alkanol wherein the alkanol is of 6 to 18 carbon atoms and wherein the number of moles of lower alkylene oxide (of 2, 3, or 4 carbon atoms) is from 3 to 12. Of such materials it is preferred to employ those wherein the higher alkanol is a higher fatty alcohol of 9 to 11 or 12 to 15 carbon atoms and which contain from 5 to 8 or 5 to 9 lower alkoxy groups per mole.

Exemplary of such compounds are those wherein the alkanol is of 12 to 15 carbon atoms and which contain about 7 ethylene oxide groups per mol, e.g., Neodol 25-7 and Neodol 23-6.5, which products are made by Shell Chemical Company, Inc. The former is a condensation product of a mixture of higher fatty alcohols averaging about 12 to 15 carbon atoms, which about 7 mols of ethylene oxide and the latter is a corresponding mixture wherein the carbon atom content of the higher fatty alcohol is 12 to 13 and the number of ethylene oxide group present averages about 6.5. The higher alcohols, are primary alkanols. Mixtures of two or more of the nonionic surfactants can be used.

Many cationic surfactants are known in the art, and almost any cationic surfactant having at least one long chain alkyl group of about 10 to 24 carbon atoms is suitable in the present invention. Such components are described in "Cationic Surfactants", Jungermann, 1970, incorporated by reference. U.S. Pat. No. 4,497,718, also incorporated by reference, describes specific cationic surfactants in detail that can be used as surfactants in the subject invention are described. As with the nonionic and anionic surfactants, the compositions of the invention may use cationic surfactants alone or in combination with any of the other surfactants known in the art. Of course, the compositions may contain no cationic surfactants at all.

Ampholytic synthetic detergents can be broadly described as derivatives of aliphatic or aliphatic derivatives of heterocyclic secondary and tertiary amines in which the aliphatic radical may be straight chain or branched and wherein one of the aliphatic substituents contains from about 8 to 18 carbon atoms and at least one contains an anionic water-solubilizing group, e.g., carboxy, sulfonate, sulfate. Examples of compounds falling within this definition are sodium 3-(dodecylamino)propionate, sodium 3-(dodecylamino)-propane-1-sulfonate, sodium 2-(dodecylamino)ethyl sulfate, sodium 2-(dimethylamino)octadecanoate, disodium 3-(N-carboxymethyldocecylamino)propane 1-sulfonate, disodium octadecyl-imminodiacetate, sodium 1-carboxymethyl-2-undecylimidazole, and sodium N,N-bis(2-hydroxyethyl)-2-sulfato-3-dodecoxypropylamine. Sodium 3-(dodecylamino) propane-1-sulfonate is preferred.

Zwitterionic surfactants can be broadly described as derivatives of secondary and tertiary amine, derivatives of heterocyclic secondary and tertiary amines, or derivatives of quaternary ammonium, quaternary phosphonium or tertiary sulfonium compounds. The cationic atom in the quaternary compound can be part of a heterocyclic ring. In all of these compounds there is at least one aliphatic group, straight chain or branched, containing from about 3 to 18 carbon atoms and at least one aliphatic substituent containing an anionic water-solubilizing group, e.g., carboxy, sulfonate, sulfate, phosphate, or phosphonate.

The compositions of this invention can also contain any other enzyme stabilizers or inhibitors. Non-limiting examples of stabilizers include glycols (e.g. monopropylene glycol) or polyols (e.g., sorbitol, glycerol), calcium ions and small carboxylic acids and salts (e.g., formic acid). Of course, the boron-scavenging properties of some common enzyme stabilizers may make their use in large amounts less desirable in this invention. Other non-limiting examples include borate esters of polyols, peptide aldehydes, fluoromethyl ketones, boronic acid, peptide boronic acids, and antioxidants. The compositions of the invention may allow the reduction or removal of other enzyme stabilizers as it is an improved technology to stabilize or inhibit enzymes. In other words, the compositions of the inventions may exclude or allow lower level of certain of the other enzyme stabilizers or include optional ingredients that are known to interact with the other enzyme stabilizers and thus that are known to destabilize enzymes. For example, the use of strong chelants, such as EDTA, DTPA or HEIDA may be compatible with the compositions of the invention. In the absence of the compound of the invention, strong chelants would complex calcium ions intended to stabilize the three-dimensional structure of the enzymes.

Polyols including vicinal diols, such as monopropylene glycol (MPG) or glycerol, are versatile ingredients that are known solvents and enzyme stabilizers. They are optional ingredients, useful at low amounts in formulations of the present invention. Monopropylene glycol may be used in the compositions of this invention in amounts of from about 0.1% to about 10%, but lower amounts, for example 0.1% to 5%, are preferred. Diols have a tendency to reduce the activity of enzymes; therefore using low the amounts of diol in a formulation is preferable. I have found that using the enzyme stabilizer of the present invention allows less diol to be used in compositions such as detergents. For example, in Example 4 significantly less glycol was used in an enzyme-stabilized liquid laundry detergent formulation. Stain removal is a test criterion for enzyme activity, and the cleaning results clearly demonstrate that reference liquid laundry detergent with high monopropylene content has a significantly poorer enzymatic stains removal than the examples of the invention. This indicates that high level of monopropylene glycol (a vicinal diol) provides a lower intrinsic activity of the enzymes.

The compositions of this invention are effective without the use of non-enzymatic proteins, such as casein, described in the earlier prior art. The complex formed by the boron-containing compound and the alpha-hydroxy-mono-carboxylic acid or it salts in this composition effectively stabilizes and/or inhibit enzymes without the additional non-enzymatic proteins.

The compositions of this invention may also contain solvents. Non-limiting and suitable solvents are described in patent application WO 2004/113484 A1. These solvents include lower alkanols with less than 7 carbons, polyols having no vicinal diols, glycol ethers based on oxides having 2 to 4 carbons and on an alkyl, aryl or substituted aryl having up to 8 carbons. Such solvents are useful in making a physically stable formulation that is essentially free of compounds that can scavenge the boron compounds at the exception of the compounds of the invention. The present invention allows formulators to lower the level of boron compounds to stabilize the enzymes by reducing the use of stabilizers that are boron scavengers.

Adjuncts suitable for incorporation into the liquid enzyme-containing product formulations of the present invention include, but are not limited to: bleaching systems, builders, dispersants, soil release agents, chelating agents, suds suppressors, softening agents, dye transfer inhibition agents, non-phosphate builders, color speckles, silver care, anti-tarnish and/or anti-corrosion agents, dyes, fillers, germicides, alkalinity sources, hydrotropes, solvents, anti-oxidants, perfumes, solubilizing agents, carriers, processing aids, pigments, and pH control agents as described in U.S. Pat. Nos. 5,705,464, 5,710,115, 5,698,504, 5,695,679, 5,686,014 and 5,646,101, and applications WO 92/19709, US 2005/0059567 A1, WO 2005/049776 A1, U.S. Pat. No. 6,803,355 B1, WO 2004/113484 A1, WO 2005/012474 A1, all of which are incorporated herein by reference.

The enzyme-stabilizing combinations of the present invention are especially of interest to make formulations having good enzyme stability that also contain ingredients that tend to complex the boron compounds not to form a reversible protease inhibitor. Such ingredients, also referred to as boron scavengers, may be of importance in the formulations, although they are known to have potential to destabilize enzymes. Examples are carbohydrates and their derivatives containing vicinal OH groups, alpha-hydroxy poly carboxylic acids, anti-wrinkling agents capable of complexing boron compounds, poly-hydroxy fatty acid amide surfactants and polyols having more than two vicinal OH groups. The enzyme-containing compositions of the present invention can tolerate the presence of boron scavengers, which can be of great importance in the application considered.

The enzyme stabilization used in the compositions of this invention achieves more effective enzyme stabilization using lower levels of enzyme stabilizers and enzymes. This improves shelf life of enzyme-containing compositions and reduces costs associated with the use of enzyme-containing compositions. A conventional protease raw material, for use such as in detergent compositions, contains about 4% active enzyme, about 60% monopropylene glycol (MPG), about 10% of enzyme stabilizers such as calcium chloride and alkali metal formates, and about 26% water, whereas the protease raw materials of this invention will typically contain lower levels of relatively expensive enzyme stabilizers and stabilizing solvents. However, a protease concentrate raw material containing about 4% active enzyme in accordance with this invention may also comprise about 1% boric acid, about 1% to 5% of an alpha-hydroxy-mono-carboxylic acid and from about 90% to about 92% water. Similarly, a conventional heavy-duty liquid detergent composition containing from about 1% to about 2% enzyme raw materials contains from about 5 to about 13% MPG, from about 1 to about 4% boric acid, about 35% actives and about 50% water. A comparable heavy-duty liquid detergent compositions in accordance with this invention may contain lower amounts of relatively expensive enzyme stabilizers/inhibitors and enzyme stabilizing solvents. In comparison heavy-duty liquid detergent formulation of this invention, containing from about 1% to about 2% enzyme raw materials may contain from about 1 to about 5% MPG, from about 1 to about 1.5% boric acid, and from about 1% to about 3% of enzyme stabilizing alpha-hydroxy-mono-carboxylic acids, along with about 35% actives and about 55 to 57% water.

The enzyme containing liquid compositions of this invention may be used in most applications where enzymes are currently added to formulations. Currently, the largest use of enzymes in household care is in fabric care. Liquid fabric care compositions of the present invention include laundry detergents, laundry pre-spotter products, and fabric softener formulations.

Other uses for stabilized enzyme-containing liquid compositions of the present invention include other household care products, personal care products, including skin-care products, and industrial products. Such personal care products include, but are not limited to, for example, hand soaps, hand sanitizers, body washes, mouth washes, toothpastes, shower gels, shampoos, body lotions, deodorants, nasal sprays and combinations thereof. A skin care product might incorporate a dermatologically-acceptable carrier to facilitate safe transfer of an enzyme to the skin. In another aspect of the present invention, the skin care product of the present invention comprises certain adjunct ingredients. Said adjuncts include, but certainly are not limited to: antimicrobial and antifungal actives, surfactants, desquamation actives, anti-acne actives, anti-wrinkle actives, anti-atrophy actives, anti-oxidants, radical scavengers, chelators, flavonoids, anti-inflammatory agents, anti-cellulite agents, topical anesthetics, tanning actives, sunscreen actives, conditioning agents, thickening agents, detackifying agents, odor control agents, skin sensates, antiperspirants and mixtures thereof. Suitable household care products, in addition to fabric care, for purposes of the present invention include, but are not limited to: hard surface cleaners, deodorizers, manual dish detergents, automatic dish detergents, floor care compositions, kitchen cleaners or disinfectants, bathroom cleaners or disinfectants and combinations thereof. Non-limiting examples of industrial uses are biofilm removal in industrial systems, food and feed industrial enzyme applications. Additional industrial applications include medical or specialty enzyme and applications such as material cleaning or disinfection.

In yet another aspect of the invention, the stabilized enzyme-containing liquid compositions of this invention may be embedded or impregnated into fiber, paper, or cloth for use. For example, the compositions may be added to a personal care wipe suitable for wiping or drying the face or hands. Other such impregnated personal care products include feminine napkins or diapers, first aid antiseptics for irritated, injured, or acne-affected skin, and wipes for pre or post-surgical use. A household care product may also take the form of a wipe or towel, suitable for household cleaning or care.

In yet another aspect of the present invention, the household care products disclosed herein comprise certain adjunct ingredients. Said adjuncts include, but certainly are not limited to: builders, bleaching agents, bleach activators, transitional metal bleach catalysts, oxygen transfer agents and precursors, soil release agents, clay soil removal and/or anti-redeposition agents, polymeric dispersing agents, brightener, polymeric dye transfer inhibiting agents, chelating agents, anti-foam agents, alkoxylated polycarboxylates, fabric softeners, perfumes, carriers, hydrotropes, processing aids, dyes or pigments, solvents solid fillers, detersive surfactants and combinations thereof.

In another preferred aspect of the present invention, the products comprising the enzyme concentrates formulated in accordance with the present invention are incorporated into a skin care product. In one aspect of the present invention, the skin care product incorporates a dermatologically acceptable carrier to facilitate safe transfer of the products comprising the enzyme cocktails formulated in accordance with the present invention to the desired area of the skin. In another aspect of the present invention, the skin care product of the present invention comprises certain adjunct ingredients. Said adjuncts include, but certainly are not limited to: antimicrobial and antifungal actives, surfactants, desquamation actives, anti-acne actives, anti-wrinkle actives, anti-atrophy actives, anti-oxidants, radical scavengers, chelators, flavonoids, anti-inflammatory agents, anti-cellulite agents, topical anesthetics, tanning actives, sunscreen actives, conditioning agents, thickening agents, detackifying agents, odor control agents, skin sensates, antiperspirants and mixtures thereof. Indeed, a complete description and examples of each of the aforementioned adjunct ingredients is set forth in U.S. Pat. No. 6,294, 186, assigned to The Procter and Gamble Company, Cincinnati, Ohio and incorporated herein by reference.

EXAMPLES

Examples of preferred and illustrative embodiments that follow are not intended to limit the scope of the invention, which is laid out in the claims. Modifications of the invention will occur to those skilled in the art and to those who make or use the invention.

Example 1

In this example several detergent compositions containing enzymes (lipase and protease) were analyzed for residual enzymes activities upon storage.

The ingredients of several heavy-duty liquid detergent compositions in accordance with this invention are set forth below in Table 1. An explanation of the abbreviations used in Table 1 and the sources of the ingredients are given below:

MEA LAS: C10-13 linear alkyl benzene sulfonic acid salt with monoethanolamine. Marlon AMX sourced from Huels AG (Schweiz)

Oleic acid: sourced from Hydrior AG

Coconut acid: C12-14 fatty acid sourced from Hydrior AG

Dobanol 45 E 7: C14-15 alkyl ethoxylate (7) from Shell Chemical Company

Citric acid: sourced from Fluka

Boric acid: sourced from Fluka

Ethanol: sourced from Fluka

MPG: monopropyleneglycol sourced from Fluka

CaCl2: Calcium Chloride sourced from Fluka

Lipolase: lipase enzyme—Lipolase 100 L sourced from Novozymes

Savinase 16 L Type EX: protease enzyme sourced from Novozymes

DL-lactic acid: sourced from Fluka

Mandelic acid: DL-mandelic acid sourced from Malinckrodt Baker by

MEA: monoethanolamine sourced from Fluka

Water: deionized water

TABLE 1

HDL Base Compositions

| | HDL1 Comparative example | HDL 2 Comparative example | HDL 3 | HDL 4 |
|---|---|---|---|---|
| MEA LAS | 18% | 18% | 18% | 18% |
| Oleic acid | 2% | 2% | 2% | 2% |
| Coconut acid | 8% | 8% | 8% | 8% |
| Dobanol 45 E7 | 10% | 10% | 10% | 10% |
| Citric acid | 3% | 3% | 3% | 3% |
| Boric acid | 1.25 | 1.25 | 1.25 | 1.25 |
| Ethanol | 1.5% | 1.5% | 1.5% | 1.5% |
| MPG | 5% | 12% | 3% | 3% |
| CaCl2 | 200 ppm | 200 ppm | 200 ppm | 200 ppm |
| Lipolase | 0.5% | 0.5% | 0.5% | 0.5% |
| Savinase 16 L Type EX | 0.5% | 0.5% | 0.5% | 0.5% |
| D,L-lactic acid | 0 | 0 | 2% | 0 |
| Mandelic acid | 0 | 0 | 0 | 2% |
| MEA to obtain pH 8 | | | | |
| Balance water to 100% | | | | |
| Residual lipase activity (%) after 1 week storage at 35° C. | 58% | 73% | 73% | 63% |
| Residual protease activity (%) after 1 week storage at 35° C. | 73% | 86% | 100% | 78% |

Method Used to Determine Residual Protease Activity:

The residual protease activity expressed in percentage versus initial protease levels was measured according to the following method: Manual Procedure for Determination of Proteolytic Activity in Detergents (Azocasein Substrate), Novo Nordisk, Biochem NH919 494 3485.

Method Used to Determine Residual Lipase Activity:

Initial lipase activity is measured using a pH-stat titration meter. The titration aqueous mixture is prepared and contains 10 mM calcium chloride, 20 mM sodium chloride, 5 mM tris buffer and 10% of a triolein substrate (Sigma lipase kit substrate 800 containing 50% triolein). The pH of the titration mixture is adjusted to about pH 8.3 to 8.6 by HCl addition. 10 to 100 microliters of the detergent compositions of the examples is added to 50 ml of the above described titration mixture. The fatty acids (oleic) formed by the lipase-catalyzed hydrolysis of the triolein substrate are titrated against a standard sodium hydroxide solution (0.025 Normal). The titration time is run up to 8 minutes. The slope of the titration curve is taken as the measure of lipase activity. Initial lipase activity is measured immediately after the detergent composition is prepared. The detergent samples are then aged at 35° C. and the residual lipase activity is measured after one week of storage. The residual lipase activity in Table 1 is reported as the percentage of the initial activity.

The above compositions were compared with conventional heavy-duty liquid detergent base composition (HDL) HDL 1 and 2, which are similar to conventional laundry detergents and are used for references. HDL 3 and 4 are non limiting formulations examples of the claimed technology. Both laundry detergents HDL 3 and HDL 4 have a higher residual protease and lipase stability upon storage than HDL 1, which contains the same amount in percentage of enzyme stabilizers as in HDL 3 & 4. HDL 2 differs from the first reference HDL 1, through the level of MPG (monopropylene glycol) which is higher (12% versus 5%). HDL 2 had a better protease and lipase residual activity than in HDL 1 due to the higher levels of MPG. HDL 2 displayed a slightly better lipase and protease residual stability versus HDL 4. However, this is largely due to its high MPG level. HDL 3 had equal residual lipase stability versus HDL 2, and higher residual protease stability than HDL 2. Thus, the liquid detergent HDL 3 of the invention is overall more robust versus HDL 2 (high level of MPG).

Example 2

This example demonstrates residual lipase and protease activity upon storage in an enzymatic premix. The ingredients of an enzymatic composition in accordance with this invention are set forth below in Table 2. An explanation of the abbreviations used in Table 2, and the ingredients sources is given below:

Lipolase 100 L: lipase enzyme sourced from Novozymes

Savinase 16 L Type EX: protease enzyme sourced from Novozymes

Boric acid: sourced from Fluka

DL-lactic acid: sourced from Fluka

The methods for residual protease and lipase activity versus time are described in EXAMPLE 1.

An enzymatic premix containing both protease and lipase was prepared. The premix contained high level of added water (above 70%). There was about a total of 7.5% monopropylene glycol in the premix from the enzymes liquid raw materials. The pH of the enzymatic premixes was adjusted to pH 6 with low level of caustic. Despite the high water level, a polar solvent, and the presence of a protease, the lipase of the premix demonstrated superior storage stability at 35° C. This demonstrates that the protease is very well inhibited and thus the protease could not degrade the already stabilized lipase present in the enzymatic premix. It also demonstrates that the anionic complex of invention stabilizes the enzymes.

TABLE 2

| Enzymatic Premix Composition | |
|---|---|
| Enzymatic Premix Composition | |
| Lipolase 100L | 10% |
| Savinase 16 KNPU | 10% |
| Boric acid | 2% |
| Lactic acid | 7.5% |
| Water containing 10 mM/L $Ca^{2+}$ (pH 6) | 70.5% |
| Residual Lipolase stability - 2 weeks at 35 C. | 98.3% |
| Residual Savinase stability - 2 weeks at 35 C. | >90% |

The residual lipase activity in EXAMPLE 2 was obtained in the presence of a lactic and boric acid contents about 4 times higher than the one of EXAMPLE 3. The residual lipase activity in the presence of a protease load about 10 times lower than the one of EXAMPLE 3 that follows.

Example 3

The residual proteolytic activities of protease concentrates were measured after storage. The ingredients of the protease concentrates combined with this invention are set forth below in Table 3. An explanation of the abbreviations used in Table 3, and the sources of the ingredients are given below:

Na Formate: Sodium Formate

CaCl2: Calcium Chloride

MPG: monopropylene glycol

Protease: a protease concentrate from GENENCOR INTERNATIONAL

Boric acid: sourced from Fluka

D,L-lactic acid: DL-lactic acid sourced from Fluka

Mandelic acid: DL-mandelic acid sourced from Malinckrodt Baker bv

The stability of a protease was evaluated with compounds of the invention and compared with a more traditional MPG based stabilization system normally used for this protease. Results of the residual protease activity, evaluated by Genencor International, of the three different samples are displayed in Table 3. The invention stabilized the protease enzyme in liquid raw materials Sample 2 and 3, which all contained about 90% of water. Enzymes normally are not stable in a high level of water. The protease residual activities displayed in Table 3 for Sample 2 and 3 compare with the residual activity of the protease in Sample 1, with water content of about 28% along. Sample 1 also contains enzyme stabilizers accounting for close to 70% of the composition.

TABLE 3

| Protease Raw Material Composition | Sample 1 comparative example | Sample 2 | Sample 3 |
|---|---|---|---|
| MPG | 60% | 0 | 0 |
| Na Formate | 8% | 0 | 0 |
| CaCl2 | 0.11% | 0 | 0 |
| Boric acid | 0 | 0.5% | 0.56% |
| D,L-lactic acid | 0 | 2.08% | 0 |
| Mandelic acid | 0 | 0 | 2.84% |
| Protease | 4% | 4% | 4% |
| Water | 27.89% | 93.42% | 92.6% |
| Residual protease after 5.5 days at 35 C. | 73% | 58% | 81% |

Example 4

Cleaning efficiency of three heavy-duty liquid laundry detergent formulations was compared, based on various enzyme stabilization/inhibition systems in accordance with the present invention. Better enzymatic stain removal is demonstrated by L-Lactic and D,L-Lactic, compared to monopropylene glycol, and can be attributed to a higher enzymatic activity.

The differences between the three formulations are explained below:

Sample 1 contains 2% D,L-Lactic acid.

Sample 2 contains 2% L-Lactic acid.

Sample 3 is a reference sample that does not contain alpha-hydroxy-mono-carboxylic acid but an additional 9% of monopropylene glycol.

The results in the Table 6 and Table 7 below indicate that Sample 1 and 2 have better stain removal efficiency than Sample 3. Moreover, Sample 2 (based on L-Lacticacid) gave on average better cleaning results than Sample 1 (based on D,L-Lactic acid) especially on enzymatic stains removal. Thus, L-Lactic acid is preferred over D,L-Lactic in the enzyme stabilization/inhibition system of the invention. Currently, L-Lactic acid has become the predominant source of lactic acid and it is likely to be today cheaper than D,L-Lactic acid.

The composition of Sample 1, 2 and 3 is given in Table 4 below:

TABLE 4

| Base A prime: | parts | | | Sample 1 % | Sample 2 % | Sample 3 % |
|---|---|---|---|---|---|---|
| Water | 30 | Base A prime | | 86.8 | 86.8 | 86.8 |
| LAS | 15.12 | MPG | | 3 | 3 | 12 |
| Oleic acid | 2 | D,L-Lactic acid | | 2 | 0 | 0 |
| Cocofatty acid | 8 | L-Lactic acid | | 0 | 2 | 0 |
| Citric acid | 3 | MEA | | 1.0 | 1.1 | 0.5 |
| Boric acid | 1.75 | Lipolase | | 0.3 | 0.3 | 0.3 |
| MEA to pH 8.0 | 8.51 | Savinase | | 0.7 | 0.7 | 0.7 |
| Dobanol 45-7 | 10 | | | — | — | — |
| Ethanol | 3 | | | | | |
| CaCl2 × 2H2O | 0.079 | | | — | — | — |
| Water | 5.34 | | | | | |
| | 86.80 | | | | | |
| | | Water | | 6.2 | 6.1 | 0 |
| | | | | 100.00 | 100 | 100.27 |

The ingredients of several heavy-duty liquid detergent compositions in accordance with this invention are set forth above in Table 4. An explanation of the abbreviations used in Table 4 and the sources of the ingredients is given below:

LAS: C10-13 linear alkyl benzene sulfonic acid. Marlon AS3 sourced from Huels AG (Schweiz)

Oleic acid: sourced from Hydrior AG

Coconut acid: C12-14 fatty acid sourced from Hydrior AG

Dobanol 45 E 7: C14-15 alkyl ethoxylate (7) from Shell Chemical Company

Citric acid: sourced from Fluka

Boric acid: sourced from Fluka

Ethanol: sourced from Fluka

MPG: monopropyleneglycol sourced from Fluka

CaCl2: Calcium Chloride sourced from Fluka

Lipolase: lipase enzyme—Lipolase 100 L sourced from Novozymes

Savinase: Savinase 16 L Type EX: protease enzyme sourced from Novozymes

D,L-lactic acid: DL-lactic acid: sourced from Fluka

L-lactic acid sourced from Fluka

MEA: monoethanolamine sourced from Fluka

Water: deionized water

The cleaning tests performed, the measurements performed, their comparisons and the statistical relevance of the results were obtained following the following guidelines/protocols:

The liquid heavy duty detergents were compared during 10 wash cycles at 40° C. cotton program and were dosed at 100 mL per wash cycle.

The following criteria of washing performance were compared: primary washing effects at 18 artificially soiled test fabrics (12 on cotton and 6 on polyester/cotton).

Testing Conditions

The washing trials were carried out in five washing machines Miele Novotronic W 985 WPS. A modified 40° C. cotton program without pre-wash with "water-plus-button" was used. To avoid effects caused by specific differences of the washing machines, the test of each product was carried out alternating in the machines (cyclic change of the machines during the test). The trials were carried out at a water-hardness of 2.5 mmol/L (i.e. 14° d German water hardness). The total load was 4.0 kg. The composition of load during the 10 wash cycles is given in the Table 5.

TABLE 5

| Composition of the load during 10 wash cycles | |
|---|---|
| Items | used as |
| 2 sheets, 6 pillow cases, 8 huckaback towels | ballast |
| 2 soil ballast fabrics wfk SBL (24 cm × 34 cm) | soil ballast |
| 4 carrier fabrics with each 18 soiled test fabrics | stain monitor |
| 2 standard cotton fabrics | monitor for evaluation of secondary washing effects and whiteness |

Primary Washing Effects

For determination of washing performance artificially soiled test fabrics (10×10) $cm^2$ are applied using four new sets of test fabrics for each wash cycle. The following test fabrics, which are fixed on four carrier fabrics, are used for:

General Detergency
  wfk-CO-pigment/sebum (Code 10 D)
  EMPA-CO-soot/mineral oil (Code 106)

Fat Removal
  wfk-CO-used motor oil (Code 10 GM)
  wfk-PES/CO-used motor oil (Code 20 GM)

Bleaching Performance
  wfk-CO-redwine (Code 90 LI)
  wfk-CO-tomato ketchup (Code 10 T)
  wfk-PES/CO-tomato ketchup (Code 20 T)
  wfk-CO-tea (Code 10 J)
  wfk-CO-blood aged (Code 10 PB)
  wfk-PES/CO-blood aged (Code 20 PB)

Enzyme Performance
  wfk-CO-pigment/oil/milk (Code 10 PPM)
  wfk-PES/CO-pigment/oil/milk (Code 20 PPM)
  wfk-PES/CO-lip stick (Code 20 LS)
  EMPA-CO-grass (Code 164)
  EMPA-CO-milk cacao (Code 112)
  wfk-PES/CO-milk cacao (Code 20 MF)
  wfk-CO-aged egg yolk (Code 10 EG)
  wfk-starch/pigment (Code 10 R)

The swatches were washed in a single wash cycle (single wash assessment), dried and ironed cautiously on the left side (the side not prone to instrumental measurement). Cleaning performance was quantified through reflectancy measurement using an automatic reflectometer (Datacolor Spectraflash SF 500, 10° observer, D 65, without gloss, with UV-filter at 420 nm) measuring the Y-value. Each fabric was measured 4 times. For each soil monitor mean and standard deviation of 160 measurements were calculated. Statistical calculation was done with T-test (two sided case) according to ISO standard 2854-1976.

Primary Washing Effects

The results of primary washing effects are given in Table 6.

TABLE 6

Primary washing effects as Y-Value - arithmetical mean of 10 wash cycles with standard deviation

| Test fabrics | Sample 1 | Sample 2 | Sample 3 |
|---|---|---|---|
| General Detergency | | | |
| wfk 10 D | 58.5 ± 4.1 | 59.3 ± 3.4 | 57.0 ± 2.6 |
| EMPA 106 | 37.0 ± 2.5 | 37.2 ± 3.1 | 34.2 ± 3.1 |
| Fat Removal | | | |
| wfk 10 GM | 50.6 ± 1.7 | 49.8 ± 1.2 | 48.8 ± 0.9 |
| wfk 20 GM | 47.2 ± 0.9 | 48.3 ± 1.0 | 46.6 ± 0.7 |
| Bleaching Performance | | | |
| wfk 90 LI | 65.4 ± 1.7 | 65.5 ± 0.9 | 65.5 ± 0.9 |
| wfk 10 T | 75.7 ± 1.4 | 75.4 ± 1.1 | 74.7 ± 1.2 |
| wfk 20 T | 76.6 ± 1.2 | 76.6 ± 0.9 | 75.9 ± 1.1 |
| wfk 10 J | 54.7 ± 2.1 | 55.0 ± 2.9 | 54.2 ± 2.8 |
| wfk 10 PB | 73.2 ± 2.2 | 74.5 ± 1.4 | 74.6 ± 1.0 |
| wfk 20 PB | 82.1 ± 1.0 | 82.8 ± 0.9 | 82.9 ± 0.9 |
| Enzyme Performance | | | |
| wfk 10 PPM | 67.4 ± 3.8 | 68.9 ± 3.0 | 64.4 ± 3.6 |
| wfk 20 PPM | 73.7 ± 2.8 | 74.9 ± 2.8 | 73.1 ± 2.5 |
| wfk 20 LS | 60.2 ± 8.3 | 62.2 ± 6.3 | 54.5 ± 6.3 |
| EMPA 164 | 64.1 ± 2.2 | 64.1 ± 2.0 | 62.6 ± 1.8 |
| EMPA 112 | 48.8 ± 3.0 | 49.7 ± 3.0 | 47.3 ± 2.6 |
| wfk 20 MF | 63.9 ± 4.3 | 64.4 ± 4.0 | 62.3 ± 3.7 |
| wfk 10 EG | 71.8 ± 2.1 | 73.2 ± 1.6 | 72.5 ± 2.5 |
| wfk 10 R | 41.6 ± 2.7 | 42.1 ± 2.4 | 40.7 ± 1.9 |

The results of statistical evaluation of primary washing effects are displayed in Table 7.

TABLE 7

Results of statistical evaluation (T-test; two sided case, 95% statistical certainty) of primary washing effect

| Test fabrics | Sample 1 versus 3 | Sample 2 versus 3 | Sample 1 versus 2 |
|---|---|---|---|
| General Detergency | | | |
| wfk 10 D | + | + | 0 |
| EMPA 106 | + | + | 0 |
| Fat Removal | | | |
| wfk 10 GM | + | + | + |
| wfk 20 GM | + | + | − |
| Bleaching Performance | | | |
| wfk 90 LI | 0 | 0 | 0 |
| wfk 10 T | + | + | + |
| wfk 20 T | + | + | 0 |
| wfk 10 J | 0 | + | 0 |
| wfk 10 PB | − | 0 | − |
| wfk 20 PB | − | 0 | − |
| Enzyme Performance | | | |
| wfk 10 PPM | + | + | − |
| wfk 20 PPM | + | + | − |
| wfk 20 LS | + | + | − |
| EMPA 164 | + | + | 0 |
| EMPA 112 | + | + | − |
| wfk 20 MF | + | + | 0 |
| wfk 10 EG | − | + | − |
| wfk 10 R | + | + | − |

Additional explanation for understanding data in Table 7, comparison sample A versus B
+ = product A is statistically significantly better than product B
0 = both products are statistically equal
− = product A is statistically significantly worse than product B Example 5

The effects of pH upon the complexation of Lactic acid with Boric acid were determined in aqueous solution. The molar ratio of lactic acid to boric acid added to the solution was varied. The formulations used at pH 8.5 are displayed in Table 8. The percentage boron measured in each of the complexes formed from the boron and lactic acid is reported for each raw material ratio at a given pH in each of Tables 9-11.

Figure 2:
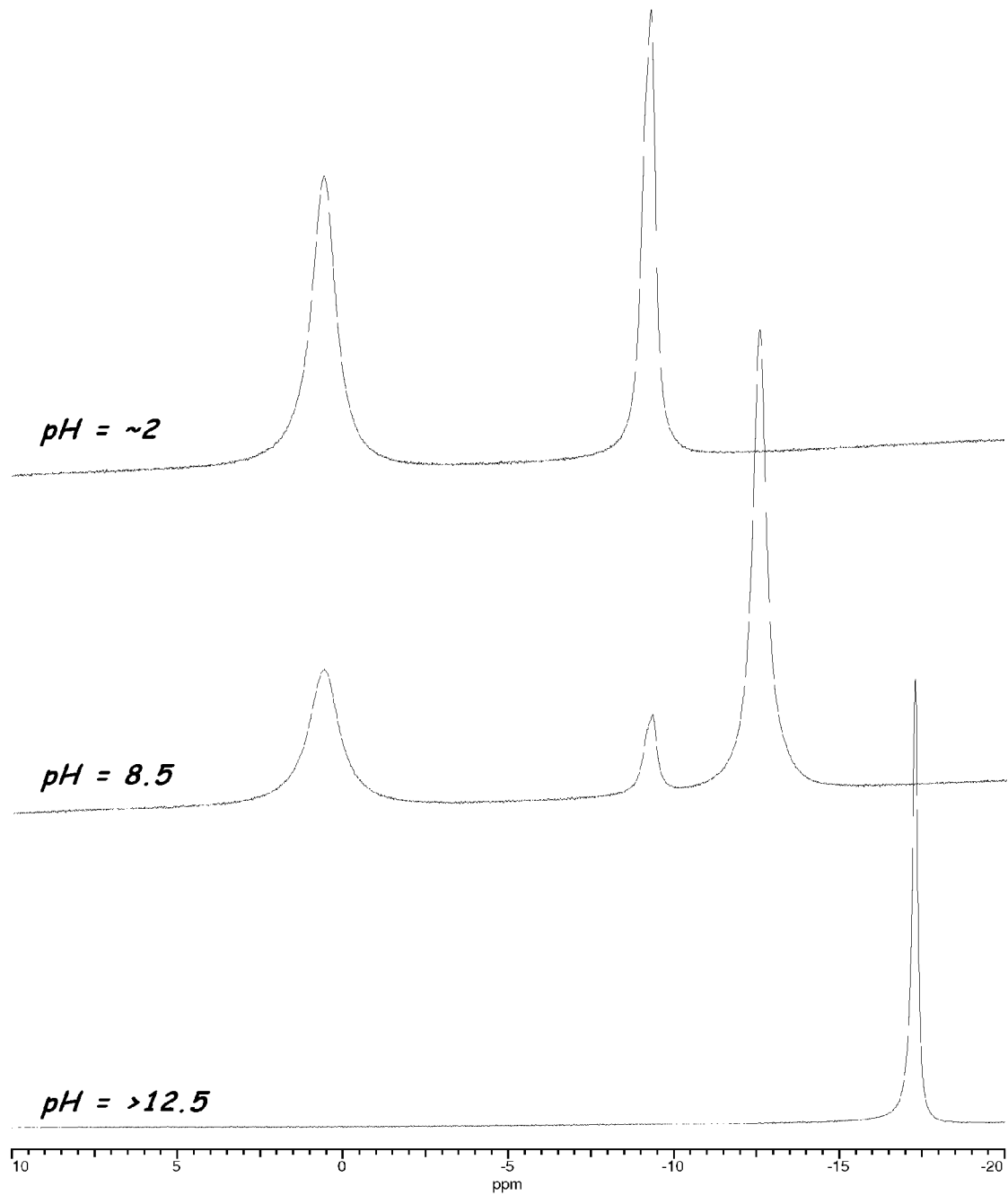
FIG. 2 shows the peaks for various boron compounds from $^{11}$B-NMR testing on four different pH solutions formed from a 0.2:0.4 ratio of boric acid to lactic acid.
Figure 3:
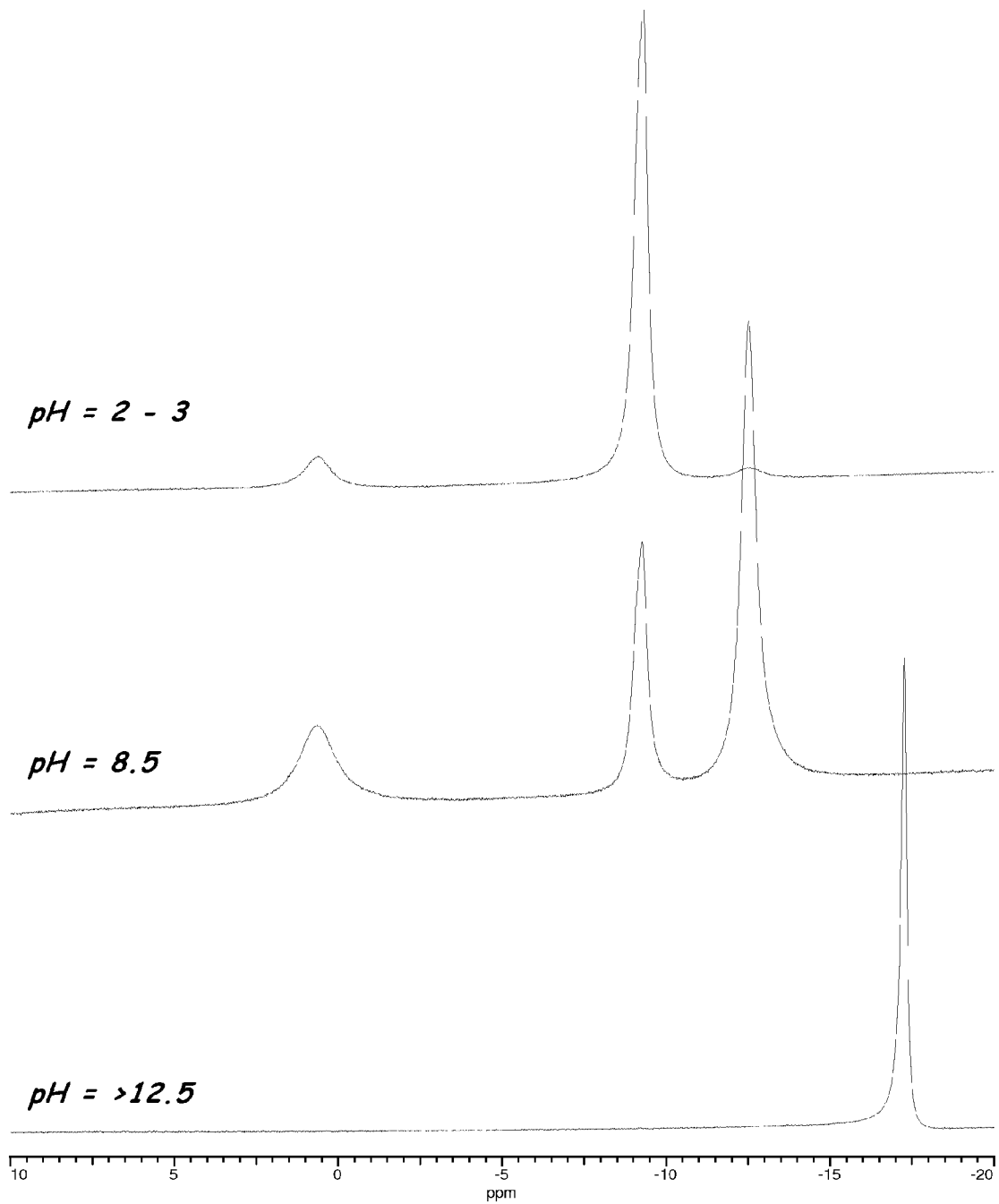
FIG. 3 shows the peaks for various boron compounds from $^{11}$B-NMR testing on four different pH solutions formed from a 0.2:0.6 ratio of boric acid to lactic acid.
Figure 4:
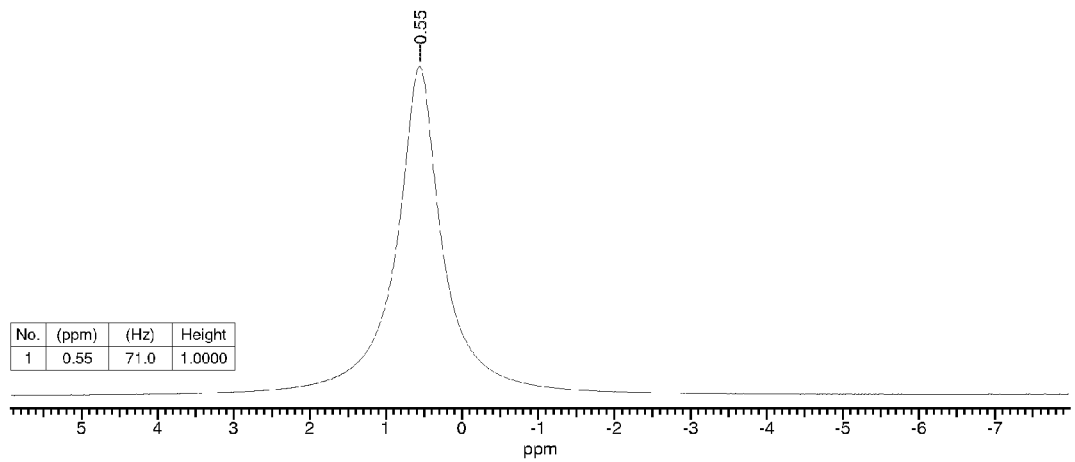
FIG. 4 shows the peak for saturated $H_3BO_3$ from $^{11}$B-NMR.

The percentage of each complex was measured by $^{11}$B-NMR with results displayed for each ratio of components added in FIGS. 1-3. FIG. 4 represents the $^{11}$B-NMR spectrum of boric acid, alone. At pH <3 the peak assigned to the [1:2]$^-$ complex surprisingly appears first. This suggests a possible pH effect of the peaks due to [1:1]$^-$ complex and [1:2]$^-$ complex exchanging places in the spectrum. However, the chemical shifts are consistent with the spectra at pH=8.5.

TABLE 8

Sample Information for pH 8.5
Number of samples: 3

| Sample Ratios | Sample Description |
|---|---|
| 0.2:0.2 | 5 ml 2M borate + 0.901 g lactic acid; pH adjusted till 8.5 +− 0.1 with NaOH or HCl, snapcap vial f 50 ml filled till mark |
| 0.2:0.4 | 5 ml 2M borate + 1.802 g lactic acid; pH adjusted till 8.5 +− 0.1 with NaOH or HCl, snapcap vial f 50 ml filled till mark |
| 0.2:0.6 | 5 ml 2M borate + 2.703 g lactic acid; pH adjusted till 8.5 +− 0.1 with NaOH or HCl, snapcap vial f 50 ml filled till mark |

For Boron NMR experiments at other pH, the pH was similarly adjusted with HCl or NaOH.

TABLE 9

Percent Boron Present at pH = 8.5 for three ratios of boric acid and lactic acid

| [B]/[lactic acid] mole/l | Boric 0.5 ppm $^{11}$B-NMR | [1:1]$^-$ complex −13 ppm $^{11}$B-NMR | 1:2 complex −10 ppm $^{11}$B-NMR | Borate −17 ppm $^{11}$B-NMR |
|---|---|---|---|---|
| 0.2:0.2 | 49 | 49 | 2 | nd |
| 0.2:0.4 | 34 | 56 | 9 | nd |
| 0.2:0.6 | 21 | 56 | 23 | nd |

TABLE 10

Percent Boron Present at pH > 12.5 for three ratios of boric acid and lactic acid

| [B]/[lactic acid] mole/l | Boric 0.5 ppm $^{11}$B-NMR | [1:1]$^-$ complex −13 ppm $^{11}$B-NMR | 1:2 complex −10 ppm $^{11}$B-NMR | Borate −17 ppm $^{11}$B-NMR |
|---|---|---|---|---|
| 0.2:0.2 | nd | nd | 5 | 95 |
| 0.2:0.4 | nd | nd | nd | >99 |
| 0.2:0.6 | nd | nd | nd | >99 |

TABLE 11

Percent Boron Present at pH < 3 for three ratios of boric acid and lactic acid

| [B]/[lactic acid] mole/l | Boric 0.5 ppm $^{11}$B-NMR | [1:1]$^-$ complex −13 ppm $^{11}$B-NMR | 1:2 complex −10 ppm $^{11}$B-NMR | Borate −17 ppm $^{11}$B-NMR |
|---|---|---|---|---|
| 0.2:0.2 (pH = ~1) | 94 | 6 | nd | nd |
| 0.2:0.4 (pH = ~2) | 56 | 44 | nd | nd |
| 0.2:0.6 (pH = ~2-3) | 11 | 86 | 3 | nd |

* Alcalase, Esperase and Savinase are trademarks of Novo Industries. Maxatase is a trademark of Pfizer Inc. Maxacal is a trademark of Gist-Brocades N.V. Maxapen is a trademark of Gist-Brocades N.V. and in the U.S. of International Biosynthetics. Lipolase and Termamyl are trademarks of Novozymes. Rapidase and Maxamyl are trademarks of DSM IP Assets B.V.

What is claimed is:

1. A liquid fabric care composition, comprising:
   protease raw material composition comprising about 90% to about 92% water and a protease enzyme reversibly inhibited by a [1:1]$^-$ complex formed from boric acid and about 1% to about 3% mandelic acid, wherein the enzyme is about 4% by weight of the protease raw material composition, wherein the protease raw material composition does not contain propylene glycol;
   wherein the pH of the liquid fabric care composition is below the pKa of the boric acid and above the pKa of the mandelic acid, and the liquid fabric care composition contains no peroxidases.

2. The liquid fabric care composition of claim 1, wherein the liquid fabric care composition is a laundry pre-spotter product.

3. The liquid fabric care composition of claim 1, wherein the liquid fabric care composition is a fabric softener formulation.

4. The liquid fabric care composition of claim 1, wherein the liquid fabric care composition is a laundry detergent.

* * * * *